(12) United States Patent
Eriksson

(10) Patent No.: US 6,468,973 B1
(45) Date of Patent: Oct. 22, 2002

(54) METHOD IN THE TREATMENT OF SCHIZOPHRENIA

(76) Inventor: Tomas Eriksson, P.O. Box 71, SE-427 22 Billdal (SE)

( * ) Notice: Subject to any disclaimer, the term of this patent is extended or adjusted under 35 U.S.C. 154(b) by 0 days.

(21) Appl. No.: 09/786,149
(22) PCT Filed: Aug. 25, 1999
(86) PCT No.: PCT/SE99/01441
§ 371 (c)(1), (2), (4) Date: Jun. 4, 2001
(87) PCT Pub. No.: WO00/12115
PCT Pub. Date: Mar. 9, 2000

(30) Foreign Application Priority Data

Aug. 26, 1998 (SE) ............................................. 9802836

(51) Int. Cl.$^7$ ........................ A61K 38/00; A61K 31/135
(52) U.S. Cl. ......................................... 514/15; 514/649
(58) Field of Search .................................. 514/629, 15

(56) References Cited

U.S. PATENT DOCUMENTS 4,474,813 A * 10/1984 Neri et al. .................. 424/324
5,091,365 A * 2/1992 Sandow et al. ................ 514/9

OTHER PUBLICATIONS

Drug Facts and Comparisons, 1998, 9$^{th}$ ed. p. 3362–3374.*
Information for Health Professionals, DECAPEPTYL CR Data Sheet [online], Jan. 30, 1997 [retrieved on Oct. 4, 2001]. Retrieved from the internet:<URL: http://www.medsave.govt.nz/Profs/Datasheet/d/decapetylcrinj.htm>, p. 1–4.*

SUPERFACT ® i (Injectable), South African Electronic Package Inserts [online], Jan. 1988 [retrieved on Oct. 4, 2001]. Retrieved from the Internet:<URL: http://home.intekom.com/pharm/hmr/suprefac.html>, p. 1–3.*

Psychoneuroendocrinology, vol. 21, No. 4, 1996, Florence Thibaut et al, "Gonadotrophin hormone releasing hormone agonist in cases of severe paraphilia: a lifetime treatment".

Dialog Information Services, File 73, Embase, Dialog accession No. 00114145, Embase accession No. 1974104246, Dein E. et al: "Antiangodrogen (cyproterone acetate) therapy in chronic schizophrenic patients".

File WPI, Derwent accession No. 98–435281, AS USSR Pharmacology RES INST: "New substituted prolyl tyrosine derivatives–having psychotropic and antidepressant action, are free from antipyramidal side effects and relatively non–toxic" Sep. 27, 1997.

Int. Pharamcopsychiat., vol. 9, 1974, M. Appelt und L. Floru, "Erfahrungen uber die Beeinflussung der Sexualitat durch Cyproteronacetat", p. 61–p. 76.

ACTA psychiatr. scand., vol. 73, 1986, M. Casas et al, "Antiandrogenic treatment of obsessive–compulsive neurosis", p. 221–p. 222.

* cited by examiner

Primary Examiner—Theodore J. Criares
Assistant Examiner—Jennifer Kim
(74) Attorney, Agent, or Firm—Orum & Roth

(57) ABSTRACT

The invention relates to the use of a composition comprising at least one substance within the group GnRH-analogues for producing a drug for treatment of schizophrenia. The invention makes it possible for patients suffering from schizophrenia to obtain partial or total relief of symptoms by treatment with a composition which comprises at least one substance within the group GnRH-analogues.

20 Claims, No Drawings

US 6,468,973 B1

METHOD IN THE TREATMENT OF SCHIZOPHRENIA

This is a 371 of PCT/SE99/01441 filed Aug. 25, 1999.

TECHNICAL FIELD

The present invention relates to the use of a composition comprising at least one substance within the group GnRH-analogues for treatment of schizophrenia.

STATE OF THE ART

Schizophrenia is a chronic psychiatric disease in which the main symptoms are delusions, hallucinations and grossly disorganised or catatonic behaviour. The disorder is chronic and often serious enough to make the patient completely or partially unable to work and live a normal life.

The disorder is described and defined in detail in The Diagnostic and Statistical Manual of Mental Disorders, fourth edition (DSM-IV) published by the American Psychiatric Association in 1994.

At the present state of the art of science, the only pharmacological treatments which are considered to be effective for the treatment of schizophrenia, are such pharmacological agents which are antagonists at the dopaminergic receptor in the brain.

That this is the present scientific opinion is evident from the following Swedish and English psychiatric textbooks.

1. Ottosson, J-O: Psykiatri. Almqvist & Wiksell Medicin Luber Utildning. Stockholm 1995. Chapter 9. Pages 167–214.
2. Gelder, M., Gath, D., Mayou, R., Cowen, P.: Oxford Textbook of Psychiatry. Oxford Medical Publications. Oxford 1995. Pages 246–293.

Physiological Regulation of Androgenic Hormones Under Normal Conditions (i.e. without Influence of Drugs)

Gonadotropin-releasing hormone (GnRH) stimulates the production of gonadotropins in the hypophysis (at the bottom of the brain). The gonadotropins are released to the blood and transported to the testes and the adrenal glands (of the male) and to the ovaries and the adrenal glands (of the female). There, the gonadotropins stimulate the synthesis and release of, among other hormones, the androgens (the male sex hormones) of which testosterone is one.

The androgenic hormones are released to the blood from the glands in which they are produced. They are transported to different organs where they exert their various actions. One of these organs is the brain. There, the androgenic hormones exert their effects by stimulating certain receptors. The androgenic activity in the brain is dependent both on the concentration of androgenic hormones in the blood, and on the density and sensitivity of the receptors on which the androgenic hormones act. The androgenic activity may thus be high, both at a high concentration of androgenic hormone in the blood, and in cases of a high density and/or sensitivity of the androgenic receptors.

The production of androgenic hormones is normally subjected to a "feed-back" regulation. If the androgenic activity in the brain is high, a compensating reduction in the synthesis and release of GnRH and consequently of the of gonadotropins takes place, with a following reduction in the synthesis and release of androgenic hormones. At a high androgenic activity in the brain, caused by a high density and/or sensitivity of the receptors (and not due to a high concentration of androgenic hormones in the blood), the compensating feed-back-regulation might cause a decrease in the synthesis and release of androgenic hormones which in turn might cause abnormally low blood concentrations of androgenic hormones. Such low concentrations could not be taken as a sign of low androgenic activity; it may still be high (if the compensation has not been sufficient) or normal (if the compensation has been sufficient).

Known Fields of Application for Pharmacological Agents which Reduce the Activity of Androgenic Hormones There are several drugs which have well-documented anti-androgenic effects. These drugs are mainly used in the treatment of carcinoma of the prostate but also in the treatment of unwanted phenomena, which are caused by a high androgenic activity. Examples of such phenomena are hypersexuality and male pattern baldness in men and hirsutism (a condition with bodily male hair growth) in women.

Groups of Drugs with Anti-androgenic Properties

Anti-androgenic effects may be obtained via three different mechanisms:

Receptor-blocking Substances

These are substances that bind to the androgenic receptors without stimulating them. In this way, the endogenous hormone is prevented from binding to the receptors with a resulting reduced androgenic activity. Preparation example: flutamide (Eulexin®).

Synthesis-inhibiting Substances

These are substances which inhibit production of androgenic hormones in the glands where they are produced. Preparation example: cyproterone acetate (Androcur®) (this substance also has receptor-blocking properties).

GnRH-analogues

These are substances which, in their effect, resemble endogenous GnRH but they produce a more powerful and more protracted effect upon the GnRH-receptors. Initially they have the same effects as endogenous GnRH, i.e. by stimulating the production of gonadotropins, the synthesis and release of androgenic hormones is also stimulated resulting in an increase in androgenic activity. After treatment during a certain period of time the sensitivity in the receptors, on which endogenous GnRH and GnRH-analogues act, will be significantly reduced. Hereby, the release of gonadotropins will also be reduced. The reduction in concentrations of circulating gonadotropins will cause a decrease in synthesis and release of androgenic hormones. Consequently, the androgenic activity in the brain and elsewhere will be dramatically reduced. Preparation example: buserelin (Suprecur®; manufacturer Hoechst Marion Roussel), leuprorelin (Enanton®; manufacturer Orion and Procren®; manufacturer Abbott), goserelin (Zoladex®; manufacturer Zeneca), triptorelin (Decapeptyl®; manufacturer Ferring).

SUMMARY OF THE INVENTION

One object of the present invention is to provide a pharmaceutical composition which enables for patients with schizophrenia to obtain partial or complete relief of symptoms by treatment with this composition.

THE SOLUTION

For this object, the invention is characterised in that the composition comprises at least one substance within the group GnRH-analogues.

Different variants of the invention are disclosed in the accompanying depending claims.

The method of treatment, described in the following, has its intellectual basis in observations that have been made in contacts with patients at a psychiatric specialist clinic, in combination with established scientific facts. To sum up, the following observations and facts are applied.

1. Remarkably many patients with schizophrenia have been found to have clinical symptoms of a high androgenic activity such as a strong sexual drive, a sebacecus skin and a male pattern baldness.
2. On the basis of observation (1) has, at the above mentioned clinic, as a clinical routine examination, the determination of the free fraction of the androgenic hormone testosterone in blood been introduced. Hereby, it has been noticed that patients suffering from serious forms of schizophrenia have subnormal blood concentrations of free testosterone. This finding has been interpreted as an effect secondary to an increased androgenic activity in the brain.
3. A patient who has been suffering from a very severe form of schizophrenia which has made him totally disabled and for which he has been receiving sickness pension for over twenty years, has after six months of treatment with the GnRH-analogue triptorelin become dramatically improved. The patient had previously been treated with various dopamine receptor antagonists without any major improvement.

The treatment of schizophrenia in accordance with the invention is performed in the following manner:

The following conditions must be fulfilled in order for the described method to be appropriate.

1. The diagnosis should be ensured in accordance with the criteria specified for example in DSM-IV.
2. Those established methods of treatment which do not cause severe side effects should first have been tried.
3. The patient should have been judged to be so severely plagued or otherwise handicapped by the disease that it is obvious that the advantage of a possible cure or relief of symptoms balances the disadvantage of the side effects of the treatment. The side effects here referred to are the reduction of the sexual drive and the reduced sexual performance which may be expected as a result of the treatment.
4. Before the pharmacological treatment starts, the patient must be subjected to a medical investigation to make certain that he/she is not suffering from any other serious disease.

In the treatment, the patient is repeatedly given a pharmacological agent from the pharmaceutical preparation group GnRH-analogues which, by decreasing the sensitivity in the receptors controlling the synthesis and release to the blood of the gonadotropins, cause a marked decrease in synthesis and release of androgenic hormones to the blood. Hereby the androgenic activity is dramatically reduced. There are several substances available on the market which cause the desired effects. There are also alternative pharmaceutical preparations available on the market. Thus, there are presently preparations for various forms of injection and for administration by nasal spray. From a general point of view it is probable that, in the treatment of schizophrenia, these pharmacological agents should be administered in the same way and in the same doses as when they are used in the treatment of carcinoma of the prostate.

One example of an administration procedure for one of these pharmacological agents is delivered in the following.

The GnRH-analogue triptorelin is available in a pharmaceutical preparation (Decapeptyl® Depot). In the use of this preparation, an injection is administered containing triptorelin embonate in a dose corresponding to 3.75 mg triptorelin. Injections with this dose are given intramuscularly. They should be repeated every fourth week from the first injection.

In order to verify that a sufficient effect has been achieved, the blood concentration of free testosterone should be assessed, e.g. once every fortnight until full effect has been established. This is the case when the blood concentration of free testosterone has fallen to levels below the detection limit or very close to it.

Initially during the treatment there is an increase in the amount of circulating androgenic hormones in the blood and consequently in androgenic activity. This increase, which may remain for some weeks, may result in a change for the worse in the psychotic symptoms. This impairment could be expected to remain until the androgenic activity has been reduced. This could be expected to take some weeks. To avoid the risk of such an initial deterioration, the patient may, during the first phase of the treatment, be treated also with the androgenic receptor-blocking agent flutamide (Eulexin®) in a dose of 250 mg administrated three times each day in tablets. These tablets are commercially available for use against carcinoma of the prostate. However, this additional treatment, is not necessary for the efficiency of the above described treatment of schizophrenia; it has the sole purpose of avoiding the risks of an initial accentuation of the symptoms.

The here described pharmacological method of treating schizophrenia implies, as in all other psychiatric treatments, that the psychiatrist provides the patient with a continuous psychological support.

Presently, it is not possible to say whether the treatment must be chronically administered, or if it could be terminated after a certain period of time without risking deterioration in schizophrenic symptoms. This question must be answered in coming clinical investigations.

EXAMPLE

A detailed case study of the treatment of a patient with a severe form of schizophrenia is disclosed in the following, as supporting evidence of the effect of the method.

A then 64 year old man consulted a psychiatric specialist about psychiatric symptoms indicating that he was suffering from schizophrenia. He had previously by other psychiatrists been given traditional treatment, for several years, without any major improvement in the symptoms of schizophrenia.

The situation when the patient came to the clinic was that he had sickness pension since more than twenty years. His contacts with other persons were highly restraint. At the initial examination of the patient, he was found to be severely ill and extremely tormented by the disease. The clinical diagnosis was that he suffered from a very serious form of schizophrenia. He had no signs of any other mental illness or personality disorder. Thus, it was a clearly defined case of schizophrenia.

Certain symptoms of androgenic hyperactivity such as a male pattern baldness and frequent sexual delusions were also found at the initial examination.

An endocrinological investigation was performed, based upon his symptoms of androgenic hyperactivity. This disclosed a low blood concentration of free testosterone. Since the patient had symptoms of androgenic hyperactivity this laboratory finding could, however, not be a symptom of a low androgenic activity. Instead, the interpretation of this laboratory finding was that it was a sign of a compensatory reduction in the synthesis and release of testosterone occurring as a consequence of an increased androgenic activity in the brain.

During long periods of time the patient had been treated with the drugs which presently are considered to have the best effect against schizophrenia.

In order to overcome the sexual delusions, treatment with the long-acting GnRH-analogue triptorelin (Decapeptyl® Depot) was given every fourth week as deep intramuscular depot injections with a dose corresponding to 1.75 mg triptorelin in each injection. Initially, he was also treated with flutamid in order to prevent a transient increase in androgenic activity. After two months treatment, the patient began to feel better. After another three months, he was dramatically better; all hallucinations had disappeared and his delusions were markedly reduced.

It is obvious that the dramatic improvement of the patient was caused by the treatment with a GnRH-analogue.

The invention is not limited to the above described embodiments, but several variants are conceivable within the scope of the accompanying claims.

What is claimed is:

1. A method for the treatment of schizophrenia comprising the steps of: administering to a patient in need thereof a drug comprising at least one substance within the group GnRH-analogues.

2. The method according to claim 1, wherein the drug is a part of a preparation which is intended for administration by means of subcutaneous injection.

3. The method according to claim 1, wherein the drug is a part of a preparation which is intended for administration by means of a nasal spray.

4. The method according to claim 1, wherein the drug is a part of a preparation which is intended for administration by means of intramuscular injection.

5. The method according to claim 1, wherein the GnRH-analogue is combined with a substance which blocks the androgenic receptors in the brain.

6. The method according to claim 5, wherein the blocking substance consists of flutamide.

7. The method according to claim 4, wherein the GnRH-analogue consists of triptorelin buserelin.

8. The method according to claim 7, wherein a dose of injection contains triptorelin embonate in a quantity corresponding to 3.75 mg triptorelin.

9. The method according to claim 7, wherein the dose of injection is intended to be repeated with an interval of about four weeks.

10. The method according to claim 1, wherein the GnRH-analogue consist of buserelin, leuprorelin or goserelin.

11. The method according to claim 2, wherein the GnRH-analogue is combined with a substance which blocks the androgenic receptors in the brain.

12. The method according to claim 3, wherein the GnRH-analogue is combined with a substance which blocks the androgenic receptors in the brain.

13. The method according to claim 4, wherein the GnRH-analogue is combined with a substance which blocks the androgenic receptors in the brain.

14. The method according to claim 5, wherein the GnRH-analogue consists of triptorelin.

15. The method according to claim 6, wherein the GnRH-analogue consists of triptorelin.

16. The method according to claim 2, wherein the GnRH-analogue consists of leuprorelin or goserelin.

17. The method according to claim 3, wherein the GnRH-analogue consists of leuprorelin or goserelin.

18. The method according to claim 4, wherein the GnRH-analogue consists of buserelin, leuprorelin or goserelin.

19. The method according to claim 5, wherein the GnRH-analogue consists of buserelin, leuprorelin or goserelin.

20. The method according to claim 6, wherein the GnRH-analogue consists of buserelin, leuprorelin or goserelin.

* * * * *